United States Patent [19]

Oloff et al.

[11] 4,199,079
[45] Apr. 22, 1980

[54] MICROSPHERE LOADING DEVICE

[75] Inventors: Clarence M. Oloff; Willi J. Buehring, both of Dayton; Kevin J. Greenlees, Fairborn, all of Ohio

[73] Assignee: The United States of America as represented by the Secretary of the Air Force, Washington, D.C.

[21] Appl. No.: 929,469

[22] Filed: Jul. 31, 1978

[51] Int. Cl.² .............................................. G01F 11/02
[52] U.S. Cl. ............................................ 222/1; 222/47
[58] Field of Search ............... 222/135, 145, 148, 440, 222/452, 47; 73/425.6, 423 A; 128/218 G, 218 C, 215, 218 R, 214 R

[56] References Cited

U.S. PATENT DOCUMENTS

| | | | |
|---|---|---|---|
| 2,496,559 | 2/1950 | Piechaczek | 128/214 B |
| 3,067,915 | 12/1962 | Shapiro et al. | 222/309 X |
| 3,817,425 | 6/1974 | Liston | 222/145 X |

*Primary Examiner*—Stanley H. Tollberg
*Attorney, Agent, or Firm*—Joseph E. Rusz; Richard J. Killoren

[57] ABSTRACT

A loading device for transferring radioactive microsphere suspensions from a storage container to test apparatus having a three way stopcock including three connectors. A 1 ml syringe is connected to one of the stopcock connectors with a 5 ml syringe being connected to a second stopcock connector. A two inch cannula hypodermic needle is connected to the third stopcock connector. The hypodermic needle has airflow passages cut in the connector portion adjacent the needle.

2 Claims, 5 Drawing Figures

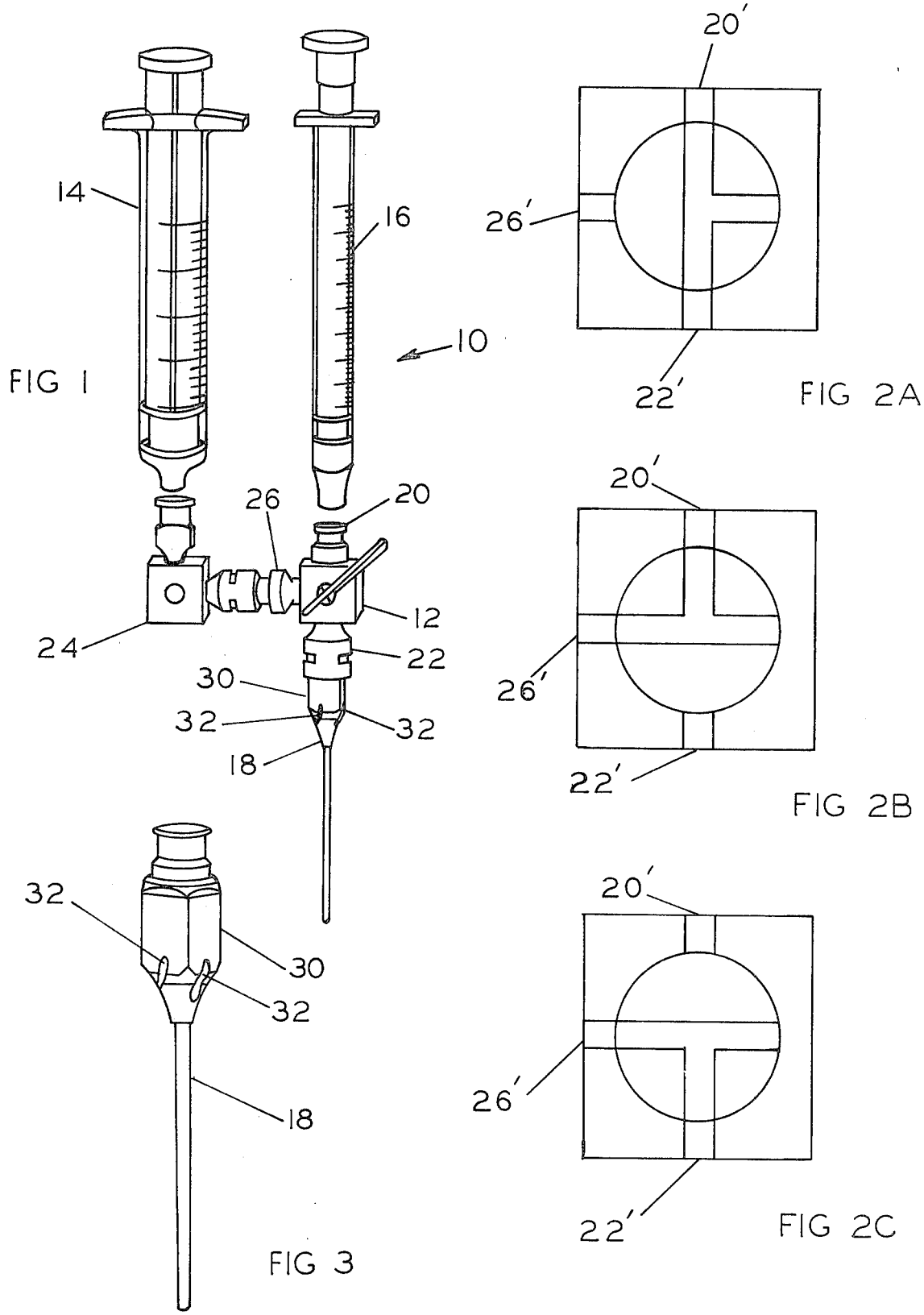

MICROSPHERE LOADING DEVICE

RIGHTS OF THE GOVERNMENT

The invention described herein may be manufactured and used by or for the Government of the United States for all governmental purposes without the payment of any royalty.

BACKGROUND OF THE INVENTION

This invention relates to a device for transferring radioactive microsphere suspensions from storage containers to test apparatus.

The measurement of blood flow to various regions of the body is used to measure performance of animals in test programs. Radioactive microspheres are used to measure blood flow to body organs and tissue. To provide accurate measurements, it is necessary to accurately measure and transfer the radioactive microsphere suspension to the test equipment.

BRIEF SUMMARY OF THE INVENTION

According to this invention, a microsphere loading device is provided wherein a three way stopcock is connected between a 1 ml loading springs, a 5 ml washing syringe and a two inch cannula hypodermic needle.

After the radioactive microsphere suspension is drawn into the 1 ml syringe and injected into the test apparatus, the 5 ml syringe is used to provide three washes for the 1 ml syringe to insure that no radioactive microspheres are left in the microsphere loading device.

IN THE DRAWING

FIG. 1 is an isometric view of the microsphere loading device of the invention.

FIG. 2A is a schematic illustration showing the three way stopcock, of FIG. 1, in the microsphere suspension transfer position.

FIG. 2B shows the three way stopcock in its wash transfer position.

FIG. 2C shows the three way stopcock in its needle flushing position.

FIG. 3 is an enlarged view of the hypodermic needle of the device of FIG. 1.

DETAILED DESCRIPTION OF THE INVENTION

Reference is now made to FIG. 1 of the drawing which shows a microsphere loading device 10, having a three way stopcock 12, a 5 ml syringe 14, a 1 ml syringe 16 and a two inch cannula hypodermic needle 18. The syringe 16 and the needle 18 are connected to the three way stopcock 12 with conventional Luer-lok connectors 20 and 22. The syringe 14 is connected to the three way stopcock by means of a connector 24 and Luer-lok 26. In the device constructed the connector 24 was a conventional three way stopcock similar to stopcock 12 but with the adjusting handle removed and the Luer-lok fitting corresponding to fitting 20 removed and with the hole plugged.

The needle connector 30 has grooves 32 provided to permit the escape of air while transferring microsphere solution and wash solution to the test apparatus.

In the operation of the device of the invention, the desired amount of radioactive suspension such as radioactive iodine, chromium, cerium, scandium or strontium in a dextran solution is drawn into the 1 ml syringe and deposited in the test apparatus. The long cannula needle permits filling the test apparatus from the bottom up to assure that no air bubbles are left in the test apparatus. The air passages 32 permit escape of air from the test apparatus during filling. After the microsphere solution is deposited into the test apparatus, the valve 12 is turned to the position shown in FIG. 2B and a wash solution such as a normal saline solution is transferred from syringe 14 to syringe 16. The level of the wash solution in syringe 16 should be higher than the level of the microsphere solution to remove any residual microsphere solution. The stopcock 12 is then turned to the position shown in FIG. 2A and the wash in syringe 16 is transferred to the test apparatus in the same manner as the microsphere solution. This procedure is then repeated for two additional washings of syringe 16 with each washing being at a higher level than the previous washing. After the three washings of syringe 16, the stopcock 12 is positioned as shown in FIG. 2C and additional washing solution is transferred to the test apparatus to provide a thorough wash for the needle 18 and to fill the test apparatus to the desired level.

The outputs 20', 22' and 26' correspond to the Luer-lok connections 20, 22 and 26 in FIG. 1. In the use of the microsphere loading device, all of the parts of the loading device were measured for residual microspheres with a gamma counter. The tests resulted in the safe transfer of a specified amount of radioactive microspheres.

There is thus provided a device for the safe and accurate loading of a radioactive microsphere solutions in test apparatus.

We claim:

1. An apparatus for transferring radioactive microsphere suspensions to test apparatus comprising: a first graduated syringe; a second graduated syringe; means connected to said first syringe and said second syringe for selectively transferring solutions from the first syringe and the second syringe to the test apparatus; said means for selectively transferring solutions from the first syringe and the second syringe to test apparatus including means for selectively transferring solution between the second syringe and the first syringe; said means for transferring solutions from the first and second syringes to test apparatus and for transferring solution between the second syringe and the first syringe including a three way stopcock having a hypodermic needle connected thereto for transferring solutions to test apparatus; said hypodermic needle including a plurality of air passage grooves in the outer surface thereof to permit passage of air from the test apparatus during transfer of solution to the test apparatus.

2. The method of transferring radioactive microsphere solution to test apparatus comprising: drawing a measured amount of radioactive microsphere solution into a first syringe; ejecting the microsphere solution from the first syringe into the test apparatus; forcing a wash solution from a second syringe into the first syringe to a higher level than the measured amount of microsphere solution in the first syringe; ejecting the wash solution from the first syringe into the test apparatus; forcing additional wash solution from the second syringe into the first syringe to a higher level than the first wash solution; ejecting the additional wash solution into the test apparatus; forcing still more wash solution from the second syringe into the first syringe to a higher level than the additional wash solution; ejecting the still more wash solution into the test apparatus; forcing wash solution from the second syringe directly into the test apparatus; providing a passage of air from the test apparatus during transfer of solution to the test apparatus.

* * * * *

UNITED STATES PATENT AND TRADEMARK OFFICE
CERTIFICATE OF CORRECTION

PATENT NO. : 4,199,079

DATED : April 22, 1980

INVENTOR(S) : Clarence M. Oloff, Willi J. Buehring and Kevin J. Greenlees

It is certified that error appears in the above-identified patent and that said Letters Patent are hereby corrected as shown below:

Col. 1, line 25, change "springs" to -- syringe --.

Signed and Sealed this

Twelfth Day of August 1980

[SEAL]

Attest:

SIDNEY A. DIAMOND

Attesting Officer

Commissioner of Patents and Trademarks